United States Patent
Williams et al.

(10) Patent No.: US 7,010,957 B2
(45) Date of Patent: Mar. 14, 2006

(54) GAS SENSORS WITH IMPROVED RESISTANCE TO HUMIDITY INTERFERENCE

(75) Inventors: David Edward Williams, Oxon (GB); Keith Francis Edwin Pratt, Oxon (GB); Peter John Smith, Oxon (GB); Dirk Niemeyer, London (GB)

(73) Assignee: City Technology Limited, Portsmouth (GB)

( * ) Notice: Subject to any disclaimer, the term of this patent is extended or adjusted under 35 U.S.C. 154(b) by 130 days.

(21) Appl. No.: 10/275,887

(22) PCT Filed: May 9, 2001

(86) PCT No.: PCT/GB01/02046

§ 371 (c)(1),
(2), (4) Date: Nov. 12, 2002

(87) PCT Pub. No.: WO01/88517

PCT Pub. Date: Nov. 22, 2001

(65) Prior Publication Data

US 2003/0074951 A1 Apr. 24, 2003

(30) Foreign Application Priority Data

May 15, 2000 (GB) .............................. 0011704

(51) Int. Cl.
*G01N 7/00* (2006.01)

(52) U.S. Cl. .................................... 73/31.05

(58) Field of Classification Search ................ 73/31.05, 73/31.06; 436/133, 134
See application file for complete search history.

(56) References Cited

U.S. PATENT DOCUMENTS 6,046,054 A * 4/2000 McGeehin et al. ......... 436/121

FOREIGN PATENT DOCUMENTS

| DE | 26 03 785 | 8/1977 |
| GB | 2 202 948 | 10/1988 |
| WO | WO 95/00836 | 1/1995 |
| WO | WO 00/24677 | 5/2000 |

OTHER PUBLICATIONS

G.S. Henshaw et al, "Selectivity and Composition Dependence of Response of Gas–sensitive Resistors," J. Mater. Chem., 1995, 5(11), 1791–1800.

Jayaraman, V. et al, "Preparation and characterisation of $Cr_{2-x}Ti_xO_{3+\delta}$ and its sensor properties," Sensors and Actuators B55 (1999) pp. 175–179.

Somiya, S. et al, "Phase Relations of the $Cr_2O_3$–$TiO_2$ System," Journal of Solid State Chemistry 25 (1978) pp. 273–284.

* cited by examiner

*Primary Examiner*—Charles Garber
(74) *Attorney, Agent, or Firm*—Steptoe & Johnson LLP

(57) ABSTRACT

Semiconductor gas-sensitive materials of the formula $Cr_{2-x}Ti_xO_3$ where $0.05 > x \geq 0.0001$, and gas sensors formed therefrom.

11 Claims, 6 Drawing Sheets

Error in Predicted CO Level for 400ppm in dry conditions (following calibration in wet conditions) due to Humidity Interference FIG. 1 Resistance of undoped $Cr_2O_3$

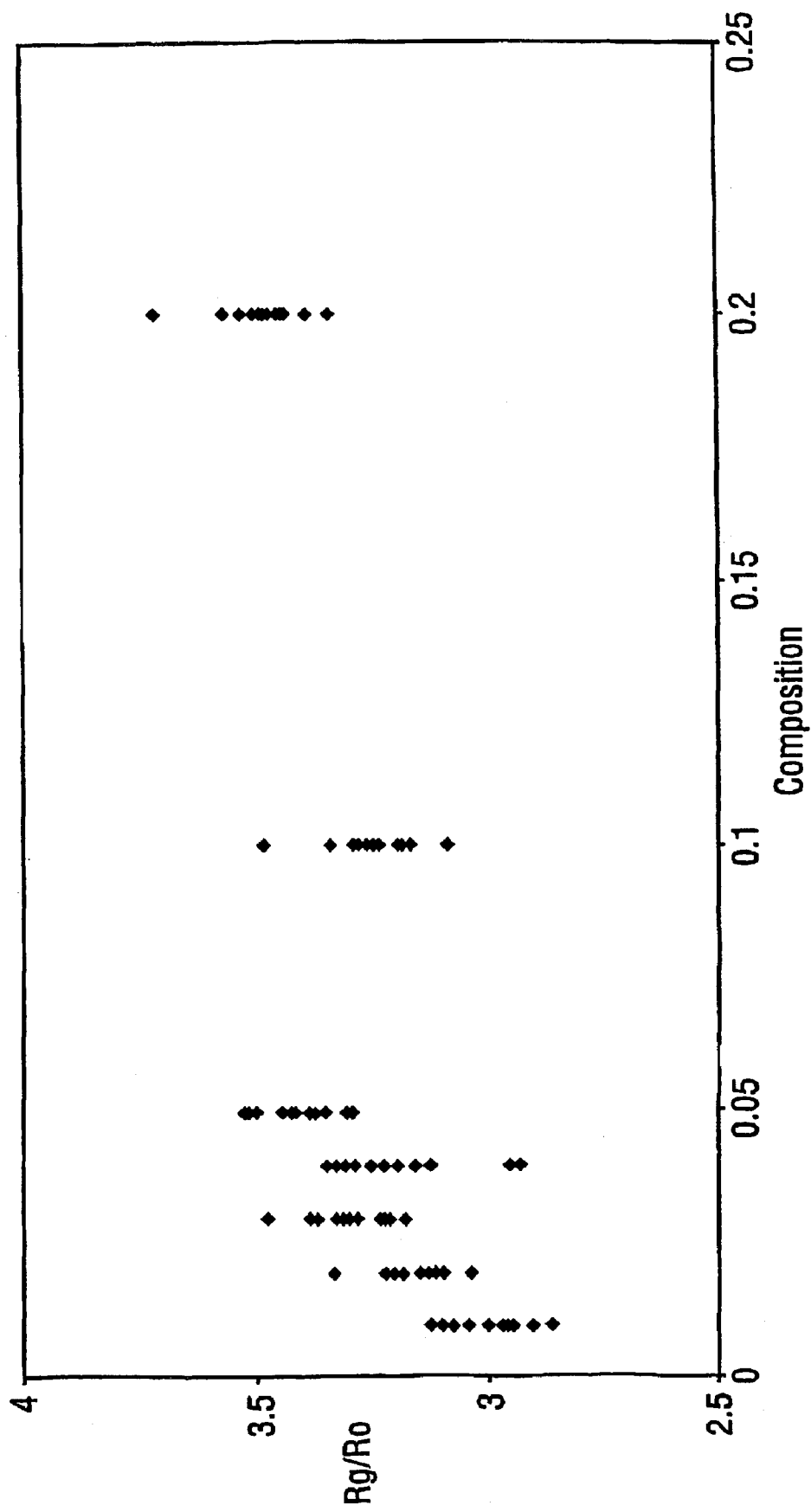

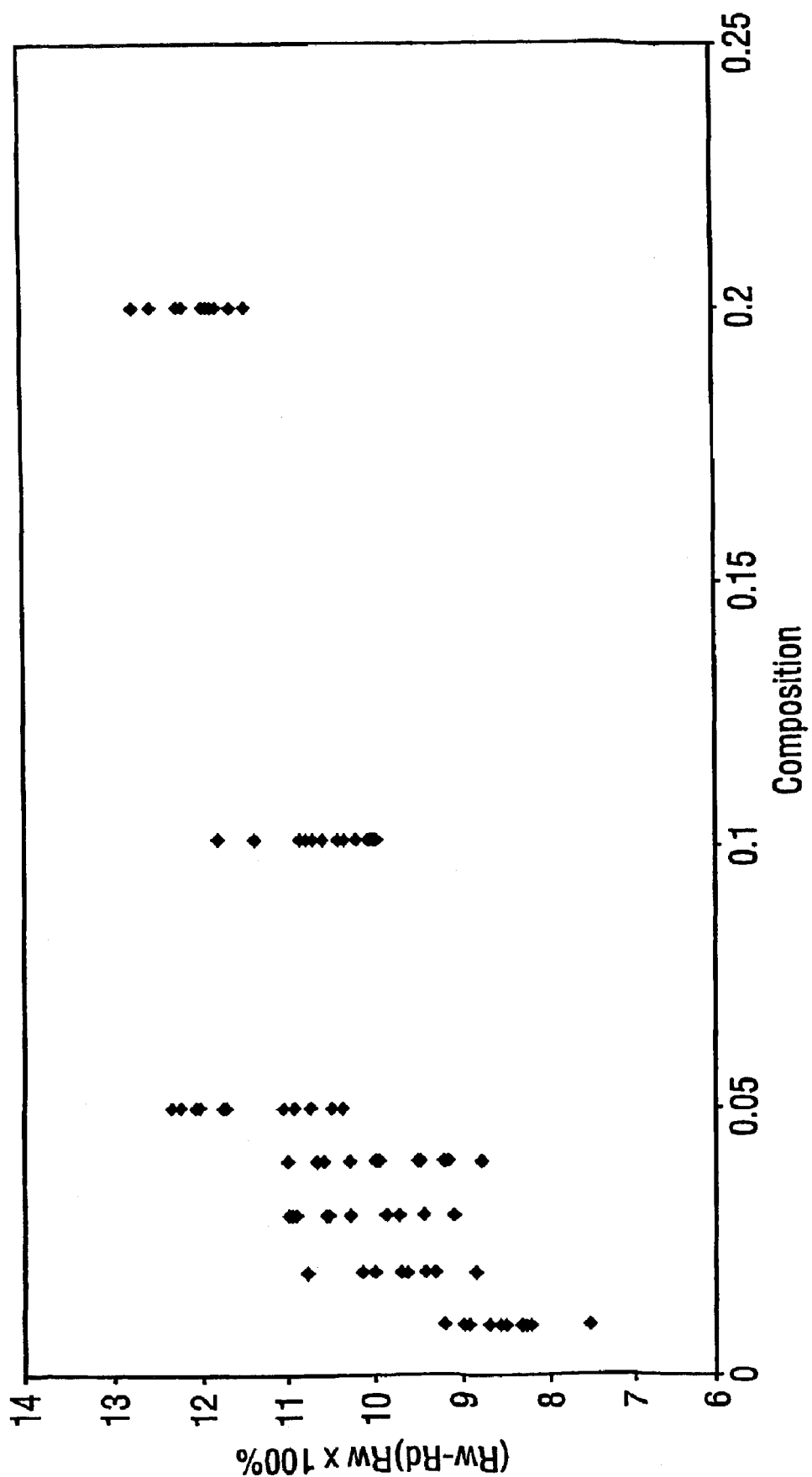
FIG. 4 Humidity Response vs Composition

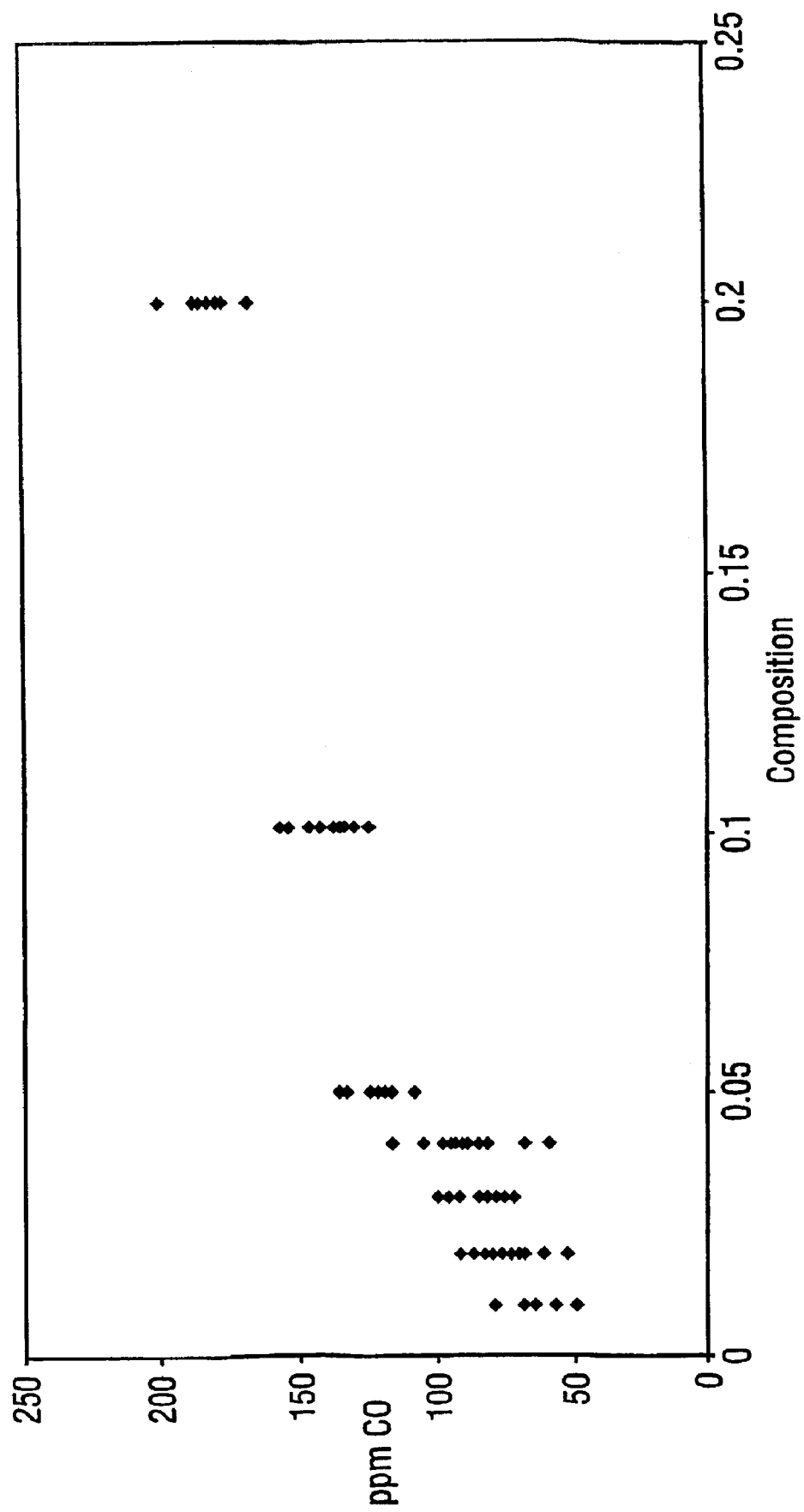
FIG. 5 Error in Predicted CO Level for 400ppm in dry conditions (following calibration in wet conditions) due to Humidity Interference

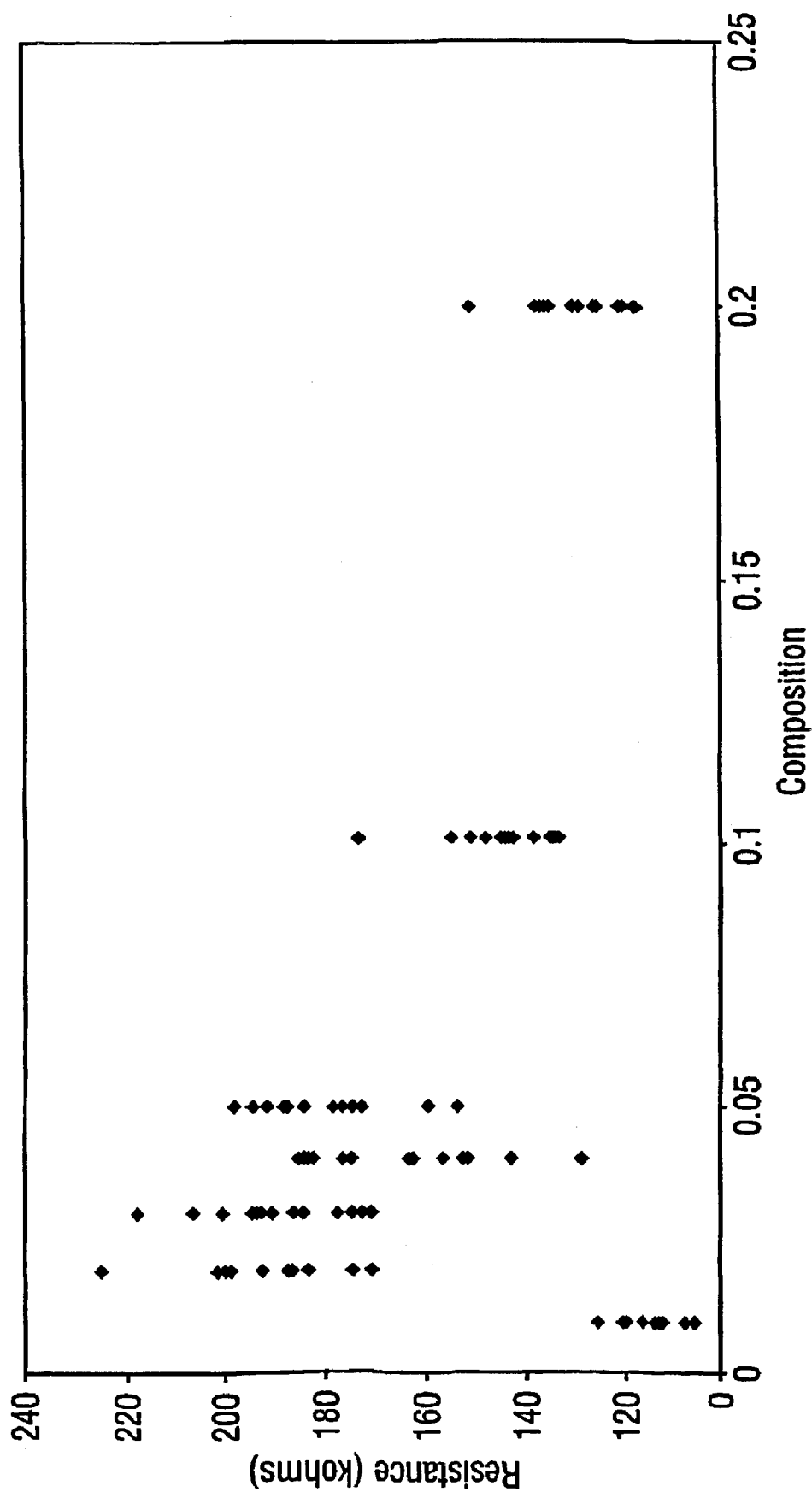

GAS SENSORS WITH IMPROVED RESISTANCE TO HUMIDITY INTERFERENCE

BACKGROUND OF THE INVENTION

Foremost amongst the many technical challenges facing manufacturers of semiconductor sensors/detectors is the need to avoid false alarms. A common cause of false alarms is the presence in the vicinity of the detector of a gas (so-called interference gas) to which the detector responds in a way similar to that for the target gas. Another cause is a change in relative humidity. It is this unfortunate sensitivity of gas-sensitive semiconductors to the vapor pressure of water that has resulted in the sensor chips being run at temperatures of 150° C. or higher. Even then, problems associated with changes in relative humidity still pertain. With increasing demands placed on the performance of carbon monoxide sensors/detectors for domestic use, there is a need to reduce the sensitivity to water vapor still further.

DESCRIPTIONS OF DRAWINGS

FIG. 3 illustrates CO Sensitivity (Rg/Ro) at 400 ppm CO vs. composition.

FIG. 4 illustrates humidity response vs. composition.

FIG. 5 illustrates error in predicted CO Level for 400 ppm in dry conditions (following calibration in wet conditions) due to humidity interference.

FIG. 6 illustrates baseline resistance vs. composition.

DETAILED DESCRIPTION OF THE INVENTION

Figure 1:
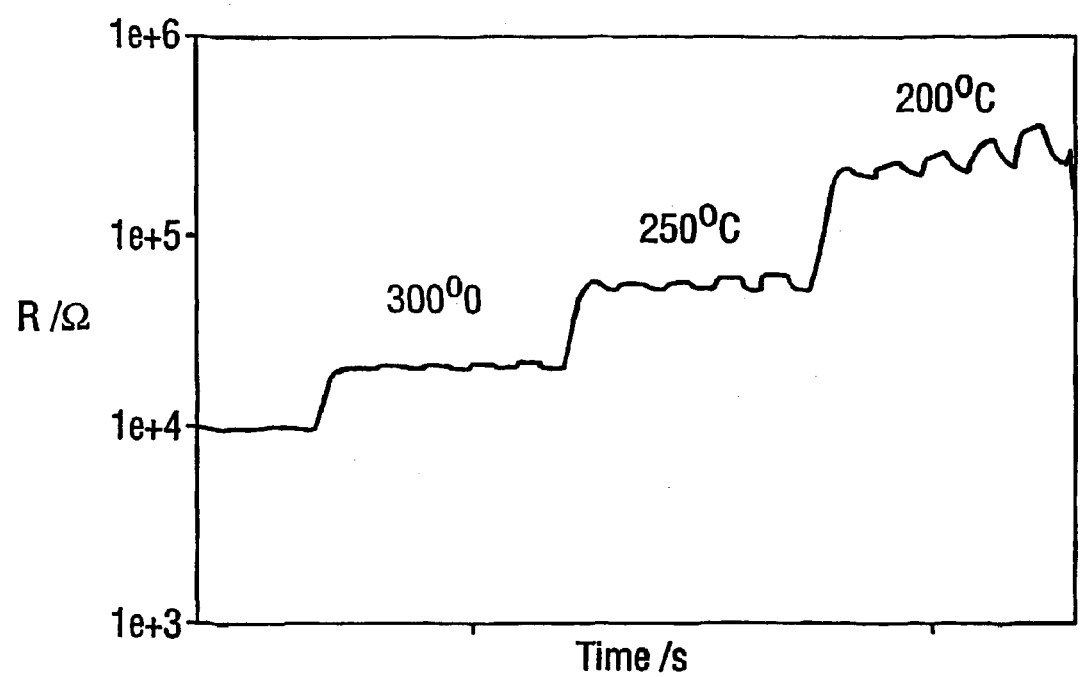
FIG. 1 illustrates resistance of undoped $Cr_2O_3$.

Pure chromium oxide, $Cr_2O_3$, is itself gas-sensitive, as demonstrated in FIG. 1. However, at the low temperatures necessary to develop a signal to a gas of interest, the response and recovery are rather slow while the effect of variation in the water vapour concentration is unacceptably large (both on the sensor resistance and on the sensitivity to other gases). These effects preclude the use of pure $Cr_2O_3$ as a gas-resistive material, since sensors for practical use are required to have respectable response/recovery times and, as mentioned above, to be reasonably resistant to relative humidity changes.

However, the presence of minor oxide additions such as $TiO_2$ have two distinct effects on $Cr_2O_3$: a significant increase in the electrical resistivity and the movement of the temperature for optimum sensitivity (for gases such as carbon monoxide) to much higher values—very desirable from a practical viewpoint. Accordingly, the system Cr—Ti—O has found use commercially as a sensor material in the detection of oxidisable organic and inorganic gases. For example, Capteur Sensors market a Carbon Monoxide sensor, NGL07, which incorporates a 90 micron thick layer of Cr—Ti—$O_3$ heated to circa 400° C.

For the compositional range, $Cr_{2-x}Ti_xO_3$ where 0.05<x<0.45, gas sensitivities are high and sensitivity to moisture is respectably low.

In this document, we will demonstrate the surprising and advantageous effects of a much lower titanium substitution in $Cr_{2-x}Ti_xO_3$. We have found that gas sensors based on the Cr—Ti—O system within the compositional window 0.05>x≧0.0001 combine the benefits of improved resistance to relative humidity changes and respectable gas sensitivities.

The teaching in the literature with regard to the chromium oxide rich region of the Cr—Ti—O system is confusing and somewhat contradictory. FIG. 91-025 in "Phase diagrams for Ceramists" suggests a solid solubility limit of x~0.06 for $TiO_2$ in $Cr_2O_3$. Somiya et al (*Journal of Solid State Chemistry* (1978), 25, pages 273–284) report a 2-phase mixture of $Cr_2O_3$ and E-phase ($Cr_2Ti_2O_7$) from~47 wt % $Cr_2O_3$ to pure $Cr_2O_3$. Both of these studies were for reaction temperatures above 1300° C. Oyama et al (*Nippon Kagaku* (1993), No. 7, pages 825–830) reported the preparation of $Cr_{2-x}Ti_xO_3$ by a vapour-phase explosive reaction. A solid solution extending up to x=0.5 was reported. Jayaraman et al (*Sensors and Actuators B*55 (1999), pages 175–179) fired mixtures of $Cr_2O_3$ and $TiO_2$ to 1000° C. and reported a solid solution with 0.1<x<0.4. The presence of $CrTiO_3$ as a minor phase was also reported. Henshaw et al (*Journal of Materials Chemistry* (1995), 5, pages 1791–1800) also reported a solid solution with x≦0.4 following firing at 1000° C.

It is well known to those skilled in the art that in the firing of ceramics, sintering competes with grain coarsening. From the viewpoint of sensitivity to gases, grain coarsening is undesirable as a reduction in surface area, and therefore catalytic activity, results. In the literature, titanium oxide is reported as a sintering aid for $Cr_2O_3$. Sintering aids promote development of the neck between grains and greater neck development should result in a reduced resistance. For pure $Cr_2O_3$, grain coarsening will dominate but as the level of $TiO_2$ addition increases, particle coarsening will become suppressed and sintering will start to dominate.

BRIEF SUMMARY OF THE INVENTION

According to a first aspect of the present invention, a semi-conductor gas-sensitive material of the formula $Cr_{2-x}Ti_xO_3$ where 0.05<x≧0.0001 is provided.

According to a second aspect of the present invention, a gas sensor for detecting reducing inorganic or organic gases comprises a semi-conductor gas-sensitive material as defined above.

According to a third aspect of the present invention a gas sensor as described above is used to sense or detect a reducing gas.

We have found that at very low levels of $TiO_2$ additions before $TiO_2$ "kicks in" as a sintering aid, it is remarkably surface active and that this surface activity contributes to an increase in gas sensitivity. Coincident with this increase in gas sensitivity is an increase in the degree of interference from humidity changes. Accordingly, a compositional window exists which provides an optimum balance between gas sensitivity and reduced humidity effects. The lower bound of this range is determined by the minimum amount of titanium required to obtain a sensor signal, which we have determined to be x≈0.0001. The upper bound is defined by the error in CO prediction caused by changes in relative humidity effects, which is x<0.05 (giving an error≦100 ppm for a 400 ppm CO gas).

DETAILED DESCRIPTION OF THE INVENTION

The following Examples support and illustrate the invention:

Example 1

Gas-Sensing Properties of Pure $Cr_2O_3$

Ultrafine chromia powder was produced from the decomposing ammonia dichromate by heating to 400° C. Pellets of 1 cm diameter and 3 mm thick were made from the powder by means of a manual press (1 tonne weight applied over surface of pellet), and fired to 1000° C. for 4 hours in air. The fired pellets were placed between two gold electrode disks in a specially constructed jig. Electrical contact between pellet and electrode was achieved by applying pressure via a spring-loaded arrangement. Gold wires spot-welded to the gold disks were fed to an ohmeter. This jig assembly was placed inside a tube-furnace and fired to 800° C. to consolidate the gold/pellet contacts and cooled to 200° C. in steps of 50° C. At each temperature interval, CO-air mixtures were introduced with the CO concentration varying from 30 ppm to 400 ppm. A measurable response to low concentrations of carbon monoxide is observable but only for rather low operation temperatures ($\leq 250°$ C). For temperatures greater than approx. 300° C., the signal is small or non-existent.

Example 2

Surface Segregation of Titanium

Figure 2:
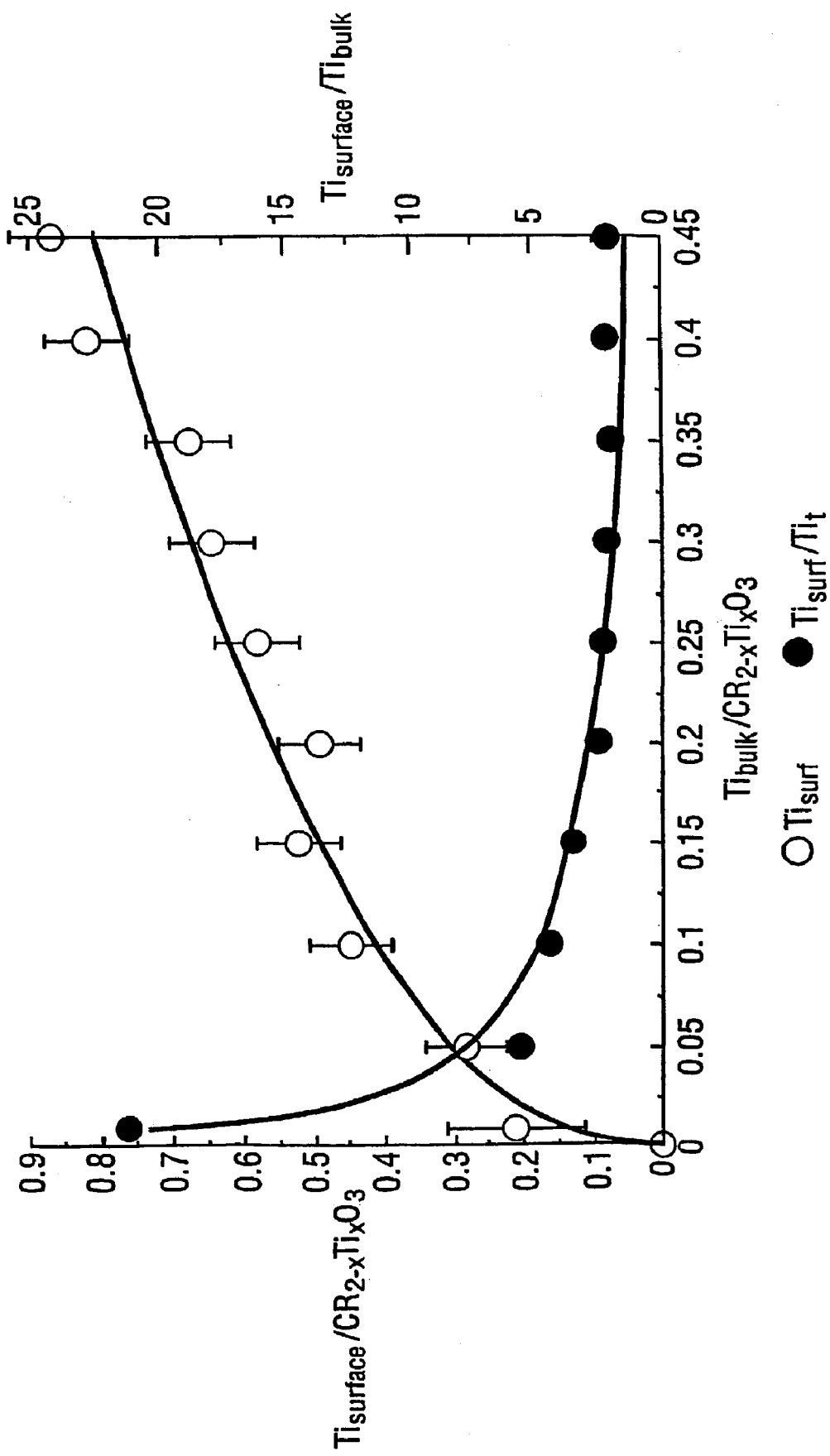
FIG. 2 illustrates surface segregation of titanium.

Mixtures of $Cr_2O_3$ and $TiO_2$ powders were weighed out to give compositions in the range $0<x<0.45$ and homogenised by ball-milling in propanol for 24 hours. The $Cr_2O_3$ was produced as described in Example 1. Pellets were prepared according to the method of Example 1. Compositional analysis of the surface of the various pellets was carried out in an ESCA VG instrument. The results are shown in FIG. 2 where the surface composition of titanium is plotted as a function of x in the starting composition. Noteworthy is that the surface segregation is most marked when values of x are very low. As x increases, the ratio $(Ti/(Ti+Cr))_{surface}/(Ti/(Ti+Cr))_{bulk}$ approaches 2, i.e. the surface composition approaches $Cr_2Ti_2O_7$ or $CrTiO_3$.

Example 3

CO Response as a Function of x where $0.01<x<0.2$

In this example, sensor devices were constructed in accordance with the construction described in Capteur Sensors data sheet for NGL07. However, the filter cap was not used and the production Cr—Ti—O layer was replaced with various $Cr_{2-x}Ti_xO_3$ layers. Starting materials of pigment-grade $Cr_2O_3$ (surface area=7 m$^2$/g) and ultrafine $TiO_2$ (surface area=55 m$^2$/g) were weighed out to give compositions in the range $0.01<x<0.2$. The mixtures were homogenised by wet-milling in propanol, sieved through a 38 micron mesh followed by calcining at 1000° C. The calcined mixtures were made into a screen-printing ink by mixing with a proprietary vehicle system supplied by ESL (Reading, UK) in the ratio 55 wt % solids : 45 wt % vehicle. The ink was printed onto an alumina tile over an interdigitated gold electrode pattern so as to give an unfired thickness of 90 microns. The underside of the tile contained a platinum serpentine track heater. The resulting structure was fired to 800° C. prior to assembling into the standard build. The sensors were powered up to approx. 400° C. in 50% RH clean air. Following stabilisation for a period of 20 minutes, the sensors were exposed to wet air (20 minutes), dry air (20 minutes), wet air (20 minutes) followed by exposure to a 400 ppm CO—clean air gas mixture at 50% RH for 20 minutes.

The ratio of sensor resistance to 400 ppm CO ($R_g^{wet}$) : sensor resistance in wet air ($R_o^{wet}$) as a function of x is shown plotted in FIG. 3.

Example 4

Humidity Response as a Function of x where $0.01<x<0.2$

As for Example 3, where the function $100\% \times ((R_o^{wet}-R_o^{dry})/R_o^{wet}))$ with $R_o^{wet}$ is the sensor resistance in wet air (50% RH) and $R_o^{dry}$ is the sensor resistance in dry air, respectively, is shown plotted as a function of x in FIG. 4.

Example 5

Error in CO Predictability as a Function of x where $0.01<x<0.2$

As for Example 3, where the error in CO predictability for 400 ppm CO in dry conditions (for sensors calibrated in wet conditions) is shown plotted as a function of x in FIG. 5. The error is calculated from the following equation:

$$Error = 400 - 400 \times D^2/W^2$$

Where $D=(R_g^{dry}/R_o^{dry}-1)^2$ and $W=(R_g^{wet}/R_o^{wet}-1)^2$ and $R_g^{dry}$ is the sensor resistance in 400 ppm CO in dry conditions.

Example 6

Baseline Resistance as a Function of x where $0.01<x<0.2$

As for Example 3, where the sensor resistance in wet air (50% RH) is plotted as a function of x in FIG. 6.

What is claimed is:

1. A semiconductor gas-sensitive material of the formula:

$$Cr_{2-x}Ti_xO_3$$

where $0.05 > x \geq 0.0001$.

2. A material according to claim 1 when in a single phase.

3. A material according to claim 2 which additionally contains one or more oxides or metals which do not degrade the sensitivity of the material.

4. A gas sensor comprising a material as claimed in claim 2 for detecting reducing inorganic or organic gases.

5. A material according to claim 1 when in more than one phase.

6. A material according to claim 5 which additionally contains one or more oxides or metals which do not degrade the sensitivity of the material.

7. A gas sensor comprising a material as claimed in claim 5 for detecting reducing inorganic or organic gases.

8. A material according to claim 1 which additionally contains one or more oxides or metals which do not degrade the sensitivity of the material.

9. A gas sensor comprising a material as claimed in claim 1 for detecting reducing inorganic or organic gases.

10. The use of a sensor as claimed in claim 9 for sensing or detecting a reducing gas.

11. The use according to claim 10 wherein the gas is CO.

* * * * *